US012616767B2

(12) United States Patent
Guggenberger

(10) Patent No.: US 12,616,767 B2
(45) Date of Patent: May 5, 2026

(54) DEVICE AND METHOD FOR RECYCLING POST-CONSUMER PLASTIC WASTE SHREDDED TO FLAKES AND WASHED

(71) Applicant: Starlinger & Co Gesellschaft m.b.H., Vienna (AT)

(72) Inventor: Jacqueline Guggenberger, Vösendorf (AT)

(73) Assignee: Starlinger & Co Gesellschaft m.b.H., Vienna (AT)

( * ) Notice: Subject to any disclaimer, the term of this patent is extended or adjusted under 35 U.S.C. 154(b) by 113 days.

(21) Appl. No.: 18/835,289

(22) PCT Filed: Jan. 22, 2023

(86) PCT No.: PCT/EP2023/051457
§ 371 (c)(1),
(2) Date: Aug. 1, 2024

(87) PCT Pub. No.: WO2023/148025
PCT Pub. Date: Aug. 10, 2023

(65) Prior Publication Data
US 2025/0161512 A1 May 22, 2025

(30) Foreign Application Priority Data

Feb. 2, 2022 (EP) .................................... 22154679

(51) Int. Cl.
*A61L 2/20* (2026.01)
*A61L 2/202* (2026.01)
(Continued)

(52) U.S. Cl.
CPC ................. *A61L 2/202* (2013.01); *A61L 2/26* (2013.01); *B29B 13/065* (2013.01); *B29B 15/00* (2013.01);
(Continued)

(58) Field of Classification Search
None
See application file for complete search history.

(56) References Cited

U.S. PATENT DOCUMENTS 9,550,132 B2    1/2017    Bergstra et al.
2009/0218052 A1*    9/2009    DeBruin ................... B29B 9/16
                                              159/47.1
(Continued)

FOREIGN PATENT DOCUMENTS

CA           601047 A      7/1960
CN      108641398 A      10/2018
(Continued)

OTHER PUBLICATIONS

"Conceptual Ozone Laundry Application Diagram", Aboslute Ozone, 1 page.
(Continued)

*Primary Examiner* — Mohammad M Ameen
(74) *Attorney, Agent, or Firm* — Workman Nydegger

(57) ABSTRACT

The device for recycling flakes from shredded and washed post-consumer plastic waste comprises—seen in the processing direction of the plastic waste—a pre-treatment unit (2) for drying and homogenising the flakes from shredded and washed post-consumer plastic waste, a melting extruder (3) for melting the plastic waste dried and homogenized in the pre-treatment unit (2), a degassing extruder (5) having a connection (5a) to a vacuum source for degassing the plastic melt, a granulating device (6) for granulating the plastic melt, and an odour removal unit (8) to subject the granules an odour removal.

Figure 1:
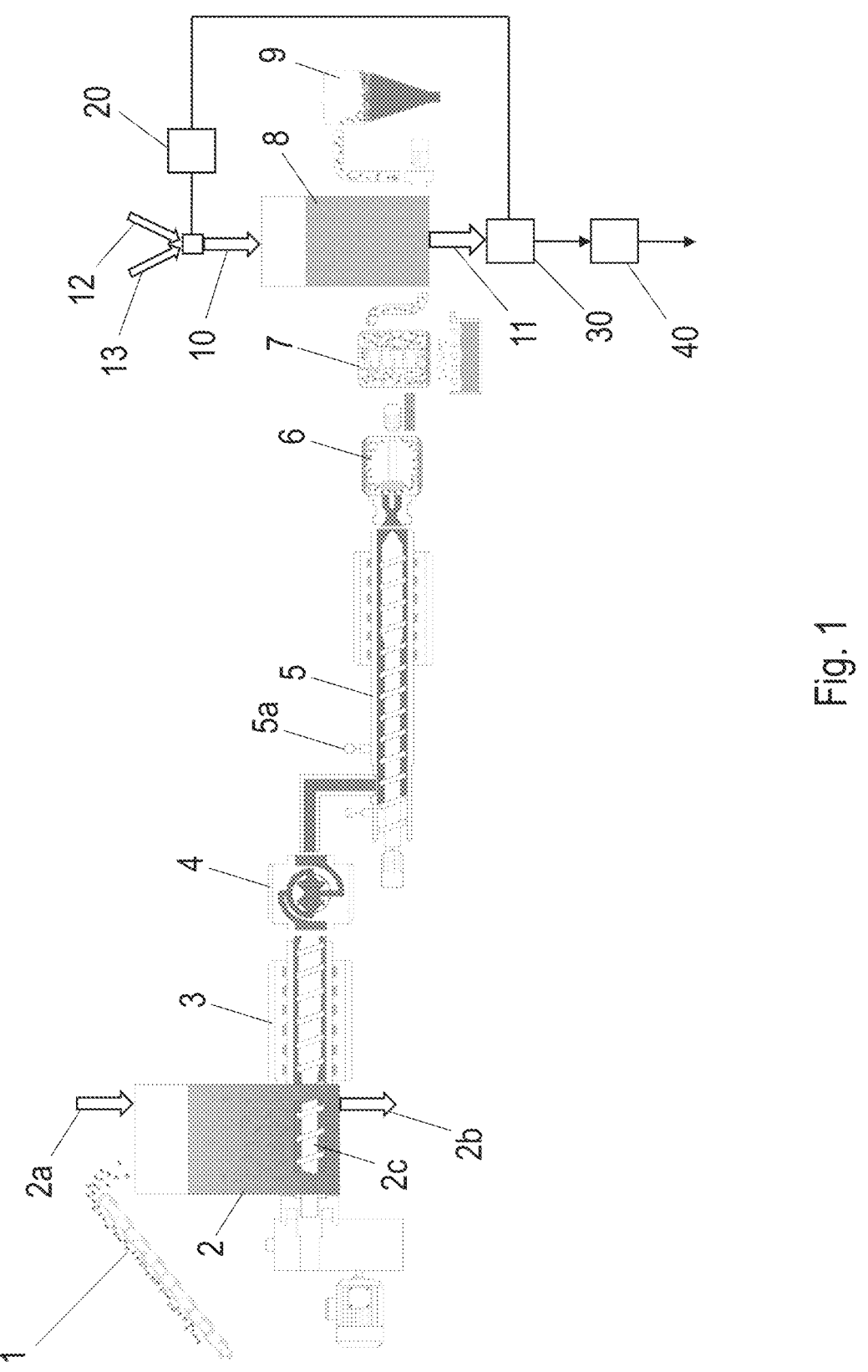

The odour removal unit (8) has a process gas feed (10) and a gas discharge (11) for discharging an exhaust gas stream, wherein the process gas feed (10) of the odour removal unit (8) is connected to an ozone source (12) or an ozone
(Continued)

generating device (13), whereby the odour removal unit (8) may be supplied with process gas enriched with ozone.

15 Claims, 2 Drawing Sheets

(51) Int. Cl.

| | |
|---|---|
| *A61L 2/26* | (2006.01) |
| *B29B 13/06* | (2006.01) |
| *B29B 15/00* | (2006.01) |
| *B29B 17/02* | (2006.01) |
| *B29B 17/04* | (2006.01) |
| *C08J 11/06* | (2006.01) |
| *B29B 13/00* | (2006.01) |
| *B29K 105/26* | (2006.01) |

(52) U.S. Cl.
    CPC .......... *B29B 17/02* (2013.01); *B29B 17/0412* (2013.01); *C08J 11/06* (2013.01); *A61L 2202/13* (2013.01); *B29B 2013/005* (2013.01); *B29B 2017/0224* (2013.01); *B29K 2105/26* (2013.01)

(56) References Cited

U.S. PATENT DOCUMENTS

| | | | | |
|---|---|---|---|---|
| 2013/0015604 A1* | 1/2013 | Hallaji | ...................... | B29B 9/16 |
| | | | | 264/234 |
| 2014/0202847 A1* | 7/2014 | Bergstra | ................... | B29B 9/16 |
| | | | | 203/96 |
| 2020/0291200 A1* | 9/2020 | Christel | .................. | C08J 11/06 |

FOREIGN PATENT DOCUMENTS

| | | | |
|---|---|---|---|
| DE | 231029 A1 | | 12/1985 |
| EP | 0602505 A1 | | 6/1994 |
| EP | 2507022 A1 | | 10/2012 |
| EP | 299 54 36 A1 | * | 3/2016 |
| EP | 3705252 A1 | | 9/2020 |
| WO | WO-2020/249256 A1 | * | 12/2020 |

OTHER PUBLICATIONS

W. Wiedmann et al., "Economic use of twin-screw extruders in recycling," (Oct. 1992), pp. 934-938.

\* cited by examiner

DEVICE AND METHOD FOR RECYCLING POST-CONSUMER PLASTIC WASTE SHREDDED TO FLAKES AND WASHED

The invention relates to a device and a method for recycling flakes from shredded and washed post-consumer plastic waste.

Re-using plastic materials plays a crucial role in terms of a sustainable recycling economy. To make this possible, it is necessary to remove odour-intensive and infectious contaminants from post-consumer plastic waste in particular. When using recycled plastic as food packaging, particularly high purity requirements are placed on the recycled plastic. It must also be ensured that taste, odour and consistency of the foodstuff are not affected in any way by their packaging obtained from recycled goods.

Recycling of post-consumer plastic waste is usually realized by shredding the waste into flakes/chopped material in a first step and then feeding it into a washing process. The washing process is preferably realized in a hot wash with the addition of caustic soda or other washing additives to clean the surface.

If a certain amount of colour purity for any further use is required, optical pre-sorting of the post-consumer plastic waste is recommended before it is shredded, if necessary, also in combination with sorting following the washing process. The flakes thus produced can then be extruded into regranulates. These regranulates are subsequently aerated using hot air for a shorter period of time (hours to days) or using ambient air for a longer period of time (days to weeks) to reduce the odour of the regranulates.

In order to make a decisive contribution to a positive eco-balance, the processing of plastic waste and its upgrading to as-new products must be as energy-saving as possible, conserve resources and the environment, and be cost-effective compared to the production of virgin material. With conventional degassing systems, the decontamination of post-consumer waste is particularly energy- and time-intensive, as the contaminated pellets are exposed to a stream of hot air for several hours or remain under vacuum. From the publication EP 2507022 B1, there have been known a method and a facility for the decontamination of plastic waste, in which flakes are extruded into pellets and the pellets thus obtained are subjected to odour reduction, by blowing hot air through an odour removal unit in which the pellets dwell.

The object of the present invention is to provide an efficient and, at the same time, environmentally friendly process for the recycling of post-consumer waste, which can provide odourless regranulate. Ideally, the present invention can improve the cleaning efficiency in the recycling of post-consumer plastics to such an extent that the recycling provides food-grade regranulate.

From the document CN 108641398 there has been known to wash plastic bottles in a special washing solution and to enrich with ozone in a mixer up to 180-220° C. Then, the plastic may be granulated.

The document CA 601047 describes the treatment of PET staple fibres and the PET film with ozone at room temperature to enable printing thereon. It has been shown that the PET material thereby remains flexible and robust, wherein a bleach effect has been observed, though. Ozone treatment was carried out in a mixture of water vapour and ozone. In tests there has been shown that treating the PET material at a temperature of 180-230° C. did not have any negative effects on the material. In the case of even higher temperatures, however, the ozone will disintegrate into oxygen.

In the document EP 0602505 there is described an ozone forming UV light radiator for treating liquids to reduce noxious substances.

Document EP 3705252 A1 describes a method for producing a plastic material from plastic waste. This method comprises selecting industrial or post-consumer plastic waste, grinding the waste, treating the waste to reduce the odour generated by waste, treating the waste for reducing the microbial load, tempering the waste in water, regranulating the waste and dehumidifying the granules. In order to reduce odour and to reduce the microbial load, there may be used ozonisation, which will not be explained in greater detail.

This known method is disadvantageous in that the treatment for reducing odour and microbial load is only performed on the ground waste. It is, however, known that in particular apolar compounds will migrate into the plastic material, see e.g. Resources, Conservation & Recycling 161 (2020), "Development and application of an analytical method to quantify odour removal in plastic waste recycling processes". During regranulation as well as during further processing of regranulate, impurities can be released, which in turn constitute an odour nuisance and therefore prevent the regranulate from being used for higher-value applications, in particular to produce packaging for foodstuffs.

Therefore, there is still a need for an efficient and at the same time environmentally friendly process for the treatment of post-consumer waste, which can provide odourless regranulate, as well as for devices to carry out this process.

The present invention solves the task posed by providing a device for recycling flakes from shredded and washed post-consumer plastic waste having the features of claim 1 and by providing a method for recycling flakes from shredded and washed post-consumer plastic waste having the features of claim 7. Embodiments of the invention are defined in the sub-claims, the description and the drawings.

The device according to the invention for recycling flakes from shredded and washed post-consumer plastic waste comprises:

a pre-treatment unit for drying and homogenizing the flakes from shredded and washed post-consumer plastic waste, a melting extruder located downstream of the pre-treatment unit for melting the plastic waste dried and homogenized in the pre-treatment unit, a degassing extruder arranged downstream of the melting extruder and having a connection to a vacuum source for degassing the plastic melt, a granulating device arranged downstream of the degassing extruder for granulating the plastic melt, an odour removal unit disposed downstream of the granulating device for subjecting the pellets to odour removal, the odour removal unit having a process gas inlet and a gas outlet for discharging an exhaust gas stream, the process gas inlet of the odour removal unit being connected to an ozone source or an ozone generating device, whereby process gas enriched with ozone can be supplied to the odour removal unit.

Thus, on the one hand, an ozone source (e.g. in the form of a gas cylinder filled with an ozone-enriched gas, e.g. ozone-enriched compressed air) can be connected to the odour removal unit. The term "ozone source" does not mean that this source provides pure ozone. On the other hand, an ozone generating device may be connected to the odour removal unit, wherein the ozone generating device draws in ambient air as process gas or takes it from the process gas inlet and enriches it with ozone by reacting the oxygen contained in the air under electrical voltage or UV radiation to form ozone.

The method according to the invention for recycling flakes from shredded and washed post-consumer plastic waste comprises:

drying and homogenizing the flakes from shredded and washed post-consumer plastic waste in a gas stream, in particular a hot gas stream, the melting of the dried and homogenized plastic waste into a plastic melt, optionally filtering out foreign matter from the molten plastic, degassing the plastic melt, granulating the molten plastic, optionally drying the granules, removing odours from the granules by a process gas stream, and enriching the process gas stream used to remove odours from the granules with ozone or providing the process gas stream as an ozone-enriched gas.

The present invention enables targeted removal of odourants from post-consumer waste. The extent of residual odours remaining from the granules produced and treated according to the invention can be determined in various ways. For example, one can have various samples of the granules evaluated in diluted or undiluted air by a panel of test persons trained to perform this task. Alternatively, material-specific indicators can be established and evaluated on the residual amount remaining after the odour removal process is complete. In addition, gas chromatographic analysis can also be used to evaluate the cleaning efficiency for individual substances.

In the recycling of post-consumer plastic waste, it is useful to arrange a melt filter between the melting extruder and the degassing extruder to remove foreign substances from the plastic melt.

If the granulating device for granulating the plastic melt is a wet granulating device, it is expedient to provide a drying device for drying the pellets, e.g. a drying centrifuge, after the granulating device, so that the pellets are fed to the odour removal unit in a substantially dry state.

Preferably, the process gas to be enriched with ozone is air, although ambient air, filtered if necessary, can also be used.

It has been shown that the ozone concentration in the enriched process gas should be at least 0.1 ppm and preferably in a range between 10 ppm and 100 ppm in order to achieve sufficient odour removal without significantly polluting the environment.

According to the invention, in order to achieve best odour removal effect, as well as to minimize ozone pollution of the environment at the same time, it is preferred to provide an adjustment device for adjusting the amount of ozone supplied to the odour removal unit, depending on the ozone concentration of the exhaust gas stream from the odour removal unit. The absolute amount of ozone is decisive for the odour removal effect, i.e. how many molecules of ozone in total impinge on the granules, and consequently the odourant molecules present (g ozone/kg plastic).

The amount of ozone supplied can be influenced by the setting device in various ways:

Either by changing the ozone concentration of the supplied process gas; or by shortening/stopping the treatment time (process duration); or by manipulating the flow rate of the process gas.

In order to carry out this adjustment as accurately, quickly and automatically as possible, the invention additionally provides an inline measuring device for measuring the ozone concentration of the exhaust gas stream from the odour removal unit, the inline measuring device controlling the adjustment device for adjusting the amount of ozone supplied to the odour removal unit as a function of the measured ozone concentration. As a result, on the one hand, sufficient ozone is produced or supplied to the process gas stream to remove odour-forming substances by oxidation, and at the same time the inline measurement and control keeps the emitted amount of ozone low. The required ozone concentration of the supplied process gas depends on the contamination intensity of the granulate or its odour intensity. If the granules are more contaminated, more ozone is consumed during treatment (reaction with the odourous substances). The remaining ozone concentration is measured at the exhaust gas stream. If a certain threshold value of the ozone concentration in the exhaust gas stream is exceeded, the amount of ozone supplied to the process gas or as process gas is throttled until the ozone concentration in the exhaust gas stream falls below the threshold value again.

Two tasks can be solved with this control:

a.) On the one hand, excess ozone should not be produced and subsequently released into the environment.

b.) On the other hand, it should be determined when the odour removal process has been completed, i.e. when the odourous substances have reacted with the ozone.

Fundamentally, the ongoing chemical process may be depicted as follows:

$$O_3 \text{ (ozone input)} + X \rightarrow O\text{---}X + O_2$$

wherein: X . . . odour substance

O—X . . . oxidized odour substance

If there are still sufficient odour substances as reactants for the ozone, the ozone can react completely and, thereby, be consumed. In the exhaust gas stream there are then present the oxidized odour substances and oxygen, indicating that the odour removal process is not yet complete.

However, if more ozone is fed with the process gas into the odour removal unit than can react with the odourous substances, the granules in the odour removal unit are loaded with, the ozone leaves the odour removal unit via the exhaust gas stream and can be measured there.

This may be simplified depicted as follows:

$$n\, O_3 \text{ (ozone input)} + X \rightarrow O\text{---}X + O_2 + (n-1)\, O_3 \text{ (ozone measurable by means of a sensor in the exhaust gas stream)}$$

wherein: $n \geq 2$

X . . . odour substance

O—X . . . oxidized odour substance

This is the case if too much ozone is fed into the odour removal unit. The following solutions are provided for this problem:

At the start of the process, process gas having low ozone concentration is introduced. If no ozone is measured in the exhaust gas stream, the ozone concentration of the process gas introduced is incrementally increased until a certain ozone concentration (e.g. a certain portion of the amount introduced) is present in the exhaust gas stream. Then, the ozone concentration of the process gas supplied is kept constant until the odour removal process has been completed, i.e. until the odour substances have been completely reacted with the ozone.

Alternatively or additionally, the flow rate of the process gas stream may be changed to adjust the amount of ozone.

This is done by starting with a certain flow rate of the process gas stream and measuring the ozone concentration in the exhaust gas stream. If there is too much ozone, the flow rate is incrementally reduced until no more ozone is measurable in the exhaust gas stream or until it drops under a certain threshold in the exhaust gas stream, respectively. Then the flow rate is kept constant until the odour removal process is completed.

During the odour removal process, the reaction ideally proceeds in such a way that the ozone is completely consumed, i.e.:

$$O_3 \text{ (ozone input)} + X \rightarrow O—X + O_2$$

wherein: X . . . odour substance

O—X . . . oxidized odour substance

As the odour removal process continues, fewer and fewer odour substance molecules are available as reactants for the ozone, and more and more ozone remains. An increase in the ozone concentration can then be measured in the exhaust gas stream.

$$n\, O_3 \text{ (ozone input)} + X \rightarrow O—X + O_2 + (n{-}1)\, O_3 \text{ (ozone}$$
measurable by means of a sensor in the exhaust gas stream)

wherein: $n \geq 2$

X . . . odour substance

O—X . . . oxidized odour substance

The completion of the odour removal process may be recognized in that there is measured a certain increase in the ozone concentration in the exhaust gas stream or in that a certain threshold (e.g. a certain portion of the ozone concentration supplied) is exceeded. As soon as this is detected, the ozone supply is immediately stopped or incrementally reduced according to the same principle as described above by either reducing the ozone concentration in the process gas supplied or by incrementally decreasing the flow rate.

It is to be noted that the reaction equations above only have illustrative purpose and are simplified, as they only show the case, in which the odour substance is oxidized only once. Actually, the most odour substances are oxidized by ozone multiple times. In other words: Two or more ozone molecules react with one odour substance molecule. The principle, however, remains the same.

The in-line measuring apparatus for measuring the ozone concentration of the exhaust gas stream from the odour removal unit may also be provided for the mere measurement of the ozone concentration, for example, in order to meet official environmental requirements or to comply with country-specific limit values.

In order to minimize environmental pollution by ozone, there is provided in an embodiment of the invention optionally at least one apparatus for the at least partial depletion of the ozone contained in the exhaust gas stream, wherein the apparatus for the depletion of ozone is configured preferably for the thermal or catalytic treatment of the exhaust gas stream or for the irradiation of the exhaust gas stream using electromagnetic waves. The electromagnetic waves are preferably UV light having a wave length of at least 254 nm.

This apparatus for the at least partial depletion of the ozone contained in the exhaust gas stream may optionally be controlled or regulated on the basis of the ozone concentration measured in the exhaust gas stream.

The invention is in the following explained in greater detail by way of exemplary embodiments with reference to the drawings.

FIG. 1 schematically shows an inventive device for recycling flakes from shredded and washed post-consumer plastic waste.

Figure 2:
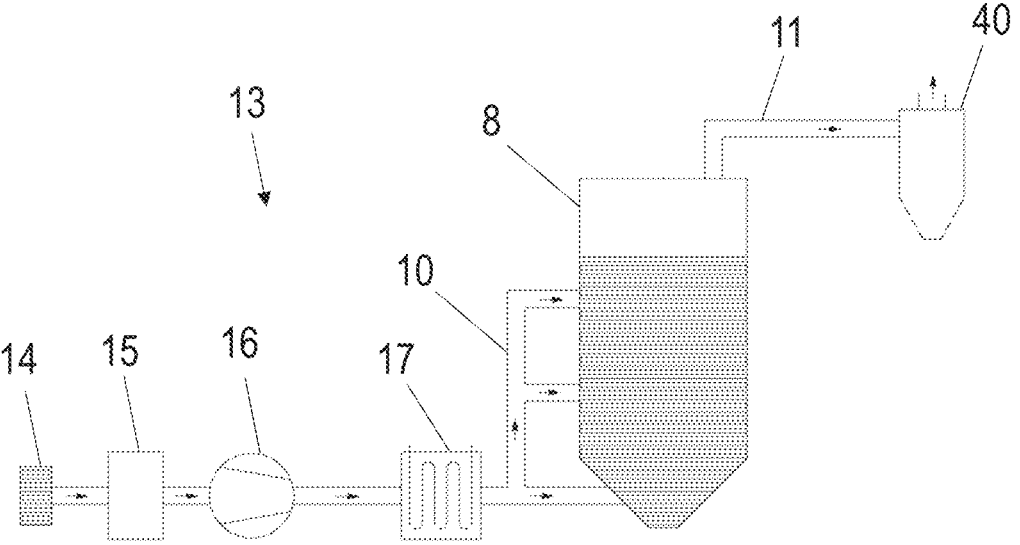

FIG. 2 shows a possible embodiment of a detail of the device of FIG. 1.

The device for recycling flakes from shredded and washed post-consumer plastic waste, which is schematically depicted in FIG. 1, has a pre-treatment unit 2 for drying and homogenizing the flakes from shredded and washed post-consumer plastic waste, wherein the feeding of the pre-treatment unit 2 with flakes is realized by a feeding unit 1 in the form of a spiral conveyor. The pre-treatment unit 2 has a gas feed 2a, which is preferably configured as a hot gas feed, and a gas discharge 2b. Gas, in particular hot air, is fed through the gas feed 2a into the pre-treatment unit 2, in which the flakes are present. Using the gas stream supplied, the flakes are being dried and homogenized. The gas stream loaded with humidity and possibly contamination is discharged through the gas discharge 2b. The discharge of the flakes from the pre-treatment unit is carried out through a spiral conveyor 2c into a plasticizing extruder 2, which is arranged downstream of the pre-treatment unit 2. In the melting extruder 3, the dried and homogenized flakes from plastic waste are melted. Downstream of the melting extruder 3, there is arranged a melt filter 4 for removing foreign matter from the plastic melt.

Downstream of the melt filter 4, a degassing extruder 5 is located having a vacuum connector 5a to a not depicted vacuum source for degassing the plastic melt, followed by a granulating device 6 for granulating the plastic melt. The granules produced in the granulating device 6 are dried in a drying centrifuge 7 and then supplied to an odour removal unit 8, where the granules are subjected to odour removal. Following the odour removal treatment, the granules are discharged from the odour removal unit 8 and may then be either directly processed or supplied to a storage silo 9.

The odour removal unit 8 has a process gas feed 10 and a gas discharge 11 for discharging an exhaust gas stream, wherein the process gas feed 10 of the odour removal unit 8 is connected to an ozone source 12, e.g. in the form of a container filled with ozone-enriched gas, e.g. ozone-enriched pressurized air, or to an ozone generating device 13, whereby ozone or ozone-enriched process gas may be supplied to the odour removal unit 8.

An adjustment device 20 serves for adjusting the amount of ozone, which is supplied to the odour removal unit 8, in dependency on the ozone concentration of the exhaust gas stream from the odour removal unit 8. Adjusting the amount of ozone to be supplied is realized, for example, by way of a control valve actuated by the adjustment device 20 in the process gas feed 10. The adjustment device 20 may be configured as an electronic control unit having a microprocessor, a main memory, a programme memory having a control algorithm stored therein and interfaces for the communication and for the actuation of actuators, such as, e.g., the control valve mentioned. The ozone generating device 13 may be configured such that it puts the ambient air under electric voltage such that the oxygen in the ambient air is reacted into ozone. The higher the electric voltage, the more ozone is generated. In this way, by controlling the electric voltage, the ozone concentration of the gas exiting the ozone generating device 13 can be controlled. The control of the ozone generating device 13 for generating and varying the electric voltage can be performed by the adjustment device 20.

Alternatively thereto, the ozone generating device 13 may operate on the basis of irradiation of aspirated ambient air with UV light, preferably having a wave length of less than 240 nm. In such an ozone generating device 13, the ozone concentration of the gas exiting the ozone generating device 13 is controlled by changing the wave length of the UV light. Also this control may be realized by using the adjustment device 20. Since UV light of shorter wave length is more energetic, therewith more ozone is produced than with irradiation using UV light of longer wave length.

The adjustment device 20 is preferably controlled by an in-line measuring apparatus 30 for measuring the ozone concentration of the exhaust gas stream from the odour removal unit 8, wherein controlling the adjustment device 20 is carried out to adjust the amount of ozone supplied to the odour removal unit 8, in dependency on the ozone concentration measured. Using such a configuration, the processes described above for the removal of odour may be carried out, while simultaneously having only little ozone-related impact onto the environment. The in-line measuring apparatus 30 can be arranged directly in or at the gas discharge 11, or it may alternatively be arranged in a distance to the gas discharge 11, but it may also have an ozone sensor, which is installed in the gas discharge 11.

At the gas discharge of the odour removal unit 8, there is optionally provided an apparatus 40 for the at least partial depletion of ozone contained in the exhaust gas stream, wherein the apparatus 40 for the depletion of ozone is configured preferably for the thermal or catalytic treatment of the exhaust gas stream or for the irradiation of the exhaust gas stream with electromagnetic waves. If the depletion of ozone by means of irradiation of the process gas removed is carried out using electromagnetic waves, then there is preferably used UV light having a wave length of at least 254 nm.

Due to its simple handling, the process gas to be enriched with ozone is preferably air. The ozone concentration in the enriched process gas should be at least 0.1 ppm and lie in a range between 10 ppm and 100 ppm.

In FIG. 2 there is schematically shown an inventive embodiment of the ozone gas generating device 13, which recovers ozone from the ambient air. This ozone gas generating device 13 comprises an air filter 14, which is connected to the ambient air and filters off dust etc. from the ambient air. The ambient air cleaned in this way is then supplied to an ozone generator 15, which, according to the principles known to those skilled in the art, converts a portion of the ambient air into ozone and, in this way, generates ozone-enriched air as process gas. The exit of the ozone generator 15 is connected to the entry, i.e. the aspiration side, of a ventilator 16. The ventilator 16, on the one side, results in the aspiration of air through the air filter 14 and the ozone generator 15 and, on the other side, blows the process gas through a heating device 17 in the process gas feed 1 and through the process gas feed 10 into the odour removal unit 8. The process gas, the ozone portion of which has been consumed by way of odour removal, exits as exhaust gas stream the odour removal unit 8 through the gas discharge 11, reaching the apparatus 40 for the depletion of ozone, where excessive ozone is being reduced. It is to be noted that the term "ozone gas generating device" is not to be understood as this device producing pure ozone. This term "ozone gas generating device" rather means that the device generates ozone-enriched gas, in particular ozone-enriched air.

In series of experiments, the process gas stream to the odour removal unit 8 was enriched with 35 ppm ozone, and in the odour removal unit 8, granules from post-consumer waste of various plastic types were each passed through with the ozone-enriched process gas for respectively 2-2.7 h. At an ozone concentration of 35 ppm and a flow rate of 1600 $m^3$ process gas/h, the ozone amount conveyed was 120 g/h. Hence, 0.24 g ozone per kg plastic was supplied.

Subsequently, in a blind test, respectively two samples of the same plastic material, wherein one sample was passed through in a conventional manner for 2-2.7 h by hot air and the other sample was passed through for the same period of time at the same temperature by hot air containing 35 ppm ozone as process gas, were presented to a board of trained odour testers for evaluation. Thereby, the granules made from HDPE, PP and LDPE and treated with ozone were assessed as being significantly superior in regard to odour intensity and hedonics by the testers than the comparative material treated exclusively with hot air.

The invention claimed is:

1. A device for recycling flakes from shredded and washed post-consumer plastic waste, comprising:
   a pre-treatment unit for drying and homogenising the flakes from shredded and washed post-consumer plastic waste,
   a melting extruder arranged downstream of the pre-treatment unit for melting the plastic waste dried and homogenized in the pre-treatment unit,
   a degassing extruder arranged downstream of the melting extruder and having a connection to a vacuum source for degassing the plastic melt,
   optionally a melt filter arranged between the melting extruder and the degassing extruder for removing foreign matter from the plastic melt,
   a granulating device arranged downstream of the degassing extruder for granulating the plastic melt,
   an odour removal unit arranged downstream of the granulating device for subjecting the granules to odour removal,
   and optionally a drying device arranged between the granulating device and the odour removal unit for drying the granules,
   characterised in that
   the odour removal unit has a process gas feed and a gas discharge for discharging an exhaust gas stream, wherein the process gas feed of the odour removal unit is connected to an ozone source or an ozone generating device, whereby the odour removal unit may be supplied with process gas enriched with ozone.

2. A device according to claim 1, further comprising an in-line measuring device for measuring the ozone concentration of the exhaust gas stream from the odour removal unit.

3. A device according to claim 1, further comprising an adjustment device for adjusting the amount of ozone, which is supplied to the odour removal unit, in dependency on the ozone concentration of the exhaust gas stream from the odour removal unit.

4. A device according to claim 1, further comprising at least one apparatus for the at least partial depletion of ozone contained in the exhaust gas stream, wherein the apparatus is configured to deplete ozone preferably for the thermal or catalytic treatment of the exhaust gas stream or for irradiating the exhaust gas stream using electromagnetic waves.

5. A device according to claim 1, wherein the process gas to be enriched with ozone is air.

6. A device according to claim 1, wherein the ozone concentration in the enriched process gas is at least 0.1 ppm.

7. A device according to claim 6, wherein the ozone concentration in the enriched process gas is in a range between 10 ppm and 100 ppm.

8. A method for recycling flakes from shredded and washed post-consumer plastic waste, comprising:

drying and homogenising the flakes from shredded and washed post-consumer plastic waste in a gas stream, in particular a hot gas stream, melting the dried and homogenized plastic waste into a plastic melt, optionally filtering out foreign matter from the plastic melt, degassing the plastic melt, granulating the plastic melt, optionally drying the granules, removing odour from the granules by way of a process gas stream, characterised by enriching the process gas stream used for removing odour from the granules with ozone or providing the process gas stream as a gas enriched with ozone.

9. A method according to claim 8, wherein the amount of ozone, which is supplied to the granules when removing the odour from the granules, is adjusted in dependency on the ozone concentration of the process gas upon removal following the odour removal treatment of the granules.

10. A method according to claim 9, wherein the ozone concentration of the process gas upon removal following the odour removal treatment of the granules is detected by way of in-line measurements and that the adjustment of the amount of ozone supplied to the granules when removing the odour from the granules is carried out in dependency on the ozone concentration measured.

11. A method according to claim 8, wherein the ozone contained in the removed process gas is depleted at least in part, wherein the depletion of ozone is preferably done by way of thermal or catalytic treatment of the process gas removed.

12. A method according to claim 8, wherein the ozone contained in the removed process gas is depleted at least in part, wherein the depletion of ozone is done by way of irradiation of the removed process gas using electromagnetic waves, wherein the electromagnetic waves are preferably UV light having a wavelength of at least 254 nm.

13. A method according to claim 8, wherein the process gas to be enriched with ozone is air.

14. A method according to claim 8, wherein the ozone concentration in the enriched process gas is at least 0.1 ppm.

15. A method according to claim 14, wherein the ozone concentration in the enriched process gas is in a range between 10 ppm and 100 ppm.

* * * * *